(12) United States Patent
Dehazya et al.

(10) Patent No.: US 6,969,531 B2
(45) Date of Patent: Nov. 29, 2005

(54) SODIUM HYALURONATE MICROSPHERES

(75) Inventors: Philip Dehazya, Westbury, NY (US); Cheng Lu, Livingston, NJ (US)

(73) Assignee: Engelhard Corporation, Iselin, NJ (US)

( * ) Notice: Subject to any disclaimer, the term of this patent is extended or adjusted under 35 U.S.C. 154(b) by 0 days.

(21) Appl. No.: 10/649,082

(22) Filed: Aug. 26, 2003

(65) Prior Publication Data

US 2004/0127459 A1 Jul. 1, 2004

Related U.S. Application Data

(63) Continuation of application No. 10/310,629, filed on Dec. 5, 2002, now abandoned, which is a continuation of application No. 09/695,445, filed on Oct. 24, 2000, now abandoned.

(51) Int. Cl.$^7$ .......................... C08B 37/00; A61K 9/50
(52) U.S. Cl. ................... 424/493; 536/54; 536/115; 536/118; 536/124; 514/54; 424/489
(58) Field of Search .................. 536/54, 115, 118, 536/124; 514/54; 424/489, 493

(56) References Cited

U.S. PATENT DOCUMENTS

| | | |
|---|---|---|
| 4,851,521 A | 7/1989 | della Valle et al. |
| 4,957,744 A | 9/1990 | della Valle |
| 5,128,326 A | 7/1992 | Balazs et al. |
| 5,616,568 A | 4/1997 | Pouyani et al. |
| 5,652,347 A | 7/1997 | Pouyani et al. |
| 5,690,954 A | 11/1997 | Illum |
| 5,766,631 A | 6/1998 | Arnold |
| 5,874,105 A | 2/1999 | Watkins et al. |
| 5,874,417 A | 2/1999 | Prestwich et al. |
| 6,071,535 A | 6/2000 | Hayward et al. |

FOREIGN PATENT DOCUMENTS

| | | |
|---|---|---|
| WO | WO 9911703 | 3/1999 |
| WO | WO 9962546 | 12/1999 |

OTHER PUBLICATIONS

Prestwich, G.D. et al, *Journal Of Controlled Release*, Elsevier Science Publishers B.V. Amsterdam, NI, (1998) 53:1–3, 93–103, XP004121260.
Goei L. et al., *Pharmaceutical Research*, (1989), 6:9, PD872.
Kyyrönen K. et al., *Intl. J. of Pharmaceutics*, (1992), 80:2,3, 161–169.
Ghezzo E. et al., *Intl. J. of Pharmaceutics*, (1992), 87:1–3, 21–29.
Pouyani T. and Prestwich G.D., *Bioconjugate Chem.*, (1994) 5:4, 339–47.
Richardson J.L. et al. *Intl. J. of Pharmaceutics*, (1995) 115:1, 9–15.
Benedetti L. et al., *Biotechnology and Bioengineering*, (1997), 53:2, 232–37.
Vercruysse K.P. et al., *Bioconjugate Chemistry*, (1997), 8:5, 686–94.

*Primary Examiner*—Dwayne Jones
(74) *Attorney, Agent, or Firm*—Melanie L. Brown

(57) ABSTRACT

The present invention relates to microspheres comprising hyaluronan derivatized with a bifunctional crosslinker to form microspheres. Methods of making such microspheres, comprising mixing hyaluronic acid and a dihydrazide with a crosslinker in an aqueous solution, adding a solvent and an emulsifying agent to form an emulsion, and lowering the pH of the emulsion to allow intramolecular and intermolecular crosslinking to occur, are also disclosed. The invention also provides for pharmaceutical or cosmetic formulations based on the microspheres described herein, further containing one or more active or cosmetic agents, and methods of using such formulations.

17 Claims, 5 Drawing Sheets

HA-ADH MICROSPHERES     25 X WATER

HA-ADH MICROSPHERES   200 X PC  BAR= 40μm

FITC MICROSPHERES - DERSICATED

FITC MICROSPHERES IN WATER

SODIUM HYALURONATE MICROSPHERES

This is a continuation of application Ser. No. 10/310,629, filed Dec. 5, 2002 now abandoned which is a continuation of application Ser. No. 09/695,445, filed Oct. 24, 2000 now abandoned. The prior application is hereby incorporated herein by reference, in its entirety.

FIELD OF THE INVENTION

The present invention relates to microspheres comprised of dihydrazide derivatives of sodium hyaluronate and a method for preparing such microspheres.

BACKGROUND OF THE INVENTION

Encapsulated pharmacological and cosmetic agents have several advantages over non-encapsulated agents. The bioavailability of the encapsulated agent can be improved, the active agent can be protected from degradation in a finished formulation, and delayed or slow, sustained release of the active agent is possible if the agent is encapsulated.

Active pharmacological or cosmetic agents can be encapsulated by incorporation into microspheres made of biocompatible, biodegradable natural polymers. A microsphere is a substantially spherical particle with a diameter in the $\mu$m range. Biocompatible, biodegradable natural polymers suitable for use in microspheres include collagen, fibrin, fibronectin, albumin, gelatin, starch, and hyaluronic acid.

Hyaluronic acid (HA) is a viscoelastic biopolymer composed of repeating disaccharide units of N-acetyl-D-glucosamine (GlcNAc) and D-glucuronic acid (GlcUA). Sodium hyaluronate is the predominate form of hyaluronic acid at physiological pH. Sodium hyaluronate and hyaluronic acid are collectively referred to as hyaluronan. Hyaluronan molecules have differing molecular weights due to the fact that the number of repeating disaccharide units in each molecule is variable. Sodium hyaluronate occurs naturally in cellular surfaces, in the basic extracellular substances of the connective tissues of vertebrates, in the synovial fluid of joints, in the vitreous humor of the eye, and in the tissue of umbilical cord. Sodium hyaluronate acts as a regulator of viscosity, tissue hydration, lubrication, and repair, and is involved in cell mobility, cell differentiation, wound healing, and cancer metastasis. Hyaluronan solutions and cross-linked hyaluronan gels can be used as drug delivery systems (U.S. Pat. No. 5,128,326). A drug can be dispersed in a hyaluronan solution, and a cross-linked hyaluronan gel can serve as a macromolecular cage in which a drug substance can be dispersed. In this manner, a hyaluronan gel or solution can serve as a vehicle that allows for the slow release of a drug that is incorporated into the gel or solution.

A large number of sodium hyaluronate derivatives have been synthesized by esterification of the carboxyl group of the D-glucuronic acid moiety of the sodium hyaluronate. (U.S. Pat. No. 4,851,521; Goei, L., et al., Pharmaceutical Research 6(9) S94 (1989); Ghezzo, E., et al., International Journal of Pharmaceutics 87: 21–29 (1992)). Ester derivatives of sodium hyaluronate have been used to form microspheres (Kyyrönen, K., et al., International Journal of Pharmacetuics 80: 161–169 (1992)); Ghezzo, E., et al., International Journal of Pharmaceutics 87:21–29 (1992); Richardson, J. L., et al., International Journal of Pharmaceutics 115: 9–15 (1995); Benedetti, L., et al., Biotechnology and Bioengineering 53: 232–237 (1997); U.S. Pat. No. 5,690,954). In addition, cross-linked esters of hyaluronic acid have been used to form microspheres, which can be incorporated into a bioabsorbable matrix to form wound implant materials (U.S. Pat. No. 5,766,631).

Sodium hyaluronate can also be derivatized by covalent attachment of hydrazides at carboxyl groups of glucuronic acid moieties (Pouyani, T. & Prestwich, G. D., Bioconjugate Chemistry 5:339–347 (1994); Vercruysse, K. P., et al., Bioconjugate Chemistry 8:686–694 (1997); U.S. Pat. No. 5,652,347, U.S. Pat. No. 5,616,568). Hyaluronate functionalized with hydrazide has a pendant hydrazide group that allows for subsequent coupling and crosslinking reactions (Pouyani, T. & Prestwich, G. D., Bioconjugate Chemistry 5:339–347 (1994); Vercruysse, K. P., et al., Bioconjugate Chemistry 8:686–694 (1997); U.S. Pat. No. 5,652,347, U.S. Pat. No. 5,616,568).

Various techniques have been used to produce microspheres made of sodium hyaluronate derivatives. A spray drying process has been used to prepare microspheres composed of sodium hyaluronate esters (Kyyronen, K., et al., International Journal of Pharmaceutics 80: 161–169 (1992)). An emulsion and solvent extraction procedure has been used to prepare microspheres composed of water-insoluble sodium hyaluronate esters (Ghezzo, E., et al., International Journal of Pharmaceutics 87: 21–29(1992)). In this approach, an emulsion was prepared in which the internal phase was a 6% w/v hyaluronate ester solution in dimethylsulphoxide (DMSO) containing the agents to be encapsulated, and the external phase consisted of mineral oil and 0.5% w/v of a surfactant. The inner phase was added to the outer phase with continuous stirring. Extraction with ethyl acetate proceeded until microspheres were formed. The microspheres were washed extensively with n-hexane and dried under a vacuum. Complete separation of the residual solvents could not be achieved with this emulsion/solvent extraction method, however, and a relevant percentage of liquid was retained within the microspheres. The presence of DMSO, ethyl acetate, and n-hexane in a composition that is to be administered to humans or animals is undesirable.

Attempts have been made to use a rapid expansion of supercritical solutions (RESS) process and a supercritical antisolvent process (SAS) to prepare microspheres composed of sodium hyaluronate benzylic esters (Bendetti, L., et al., Biotechnology and Bioengineering 53: 232–237 (1997)). In the RESS process, a supercritical fluid is used to solubilize a nonvolatile solute. The resulting solution is highly compressible and a sharp decrease in the solvent density, which can be obtained by a relatively small change in pressure, leads to a large decrease in the solubility of the solute. Solute nucleation, triggered by a sudden pressure decrease, is performed in media in which high supersaturation ratios are uniformly reached, which can lead to the formation of microparticles.

The SAS process is performed by first dissolving a solid of interest in an organic liquid (DMSO). Then, the supercritical fluid ($CO_2$), which is not able to dissolve the solid but is completely miscible with the liquid, is added to the solution in order to precipitate the solute. The SAS continuous process is performed in the critical region of the $CO_2$-DMSO system. The SAS batch process involves a low pressure gradient value and a uniform distribution of the antisolvent in the liquid.

The RESS process could not be used to prepare hyaluronic acid benzylic ester microspheres because the solubility of the hyaluronic acid ester in $CO_2$ was too low (Bendetti, L., et al., Biotechnology and Bioengineering 53: 232–237 (1997)). Using the SAS continuous process, appreciable amounts of solute were produced, but the particles formed were not regular in shape and morphology, and agglomerate structures were obtained. When the SAS process was carried out in a batch mode, microspheres of the sodium hyaluronate ester were obtained that had an average diameter of 0.4 µm and a narrow particle size distribution.

To date, the art has not provided a hydrophilic hyaluronic acid microsphere, e.g., that may be useful for delivery of a pharmaceutical or cosmetic.

SUMMARY OF THE INVENTION

The present invention relates to microspheres comprising hyaluronan functionalized with a homobifunctional crosslinker at glucuronic acid sites of the hyaluronan, wherein the derivitized hyaluronan is crosslinked intramolecularly and intermolecularly in the form of a microsphere.

In another aspect, the invention relates to a method of making a functionalized hyaluronic acid microsphere comprising mixing hyaluronic acid and a dihydrazide with a crosslinker in an aqueous solution, adding a solvent and an emulsifying agent to form an emulsion, and lowering the pH of the emulsion to allow intramolecular and intermolecular crosslinking to occur.

In yet another aspect, the invention relates to a pharmaceutical or cosmetic formulation comprising a pharmacologically effective amount of said microspheres and an acceptable carrier, excipient, or diluent.

In a further aspect, the invention relates to a method of administering microspheres to a human or animal comprising administering a pharmacologically effective amount of said pharmaceutical or cosmetic formulation.

DETAILED DESCRIPTION OF THE INVENTION

Figure 1A:
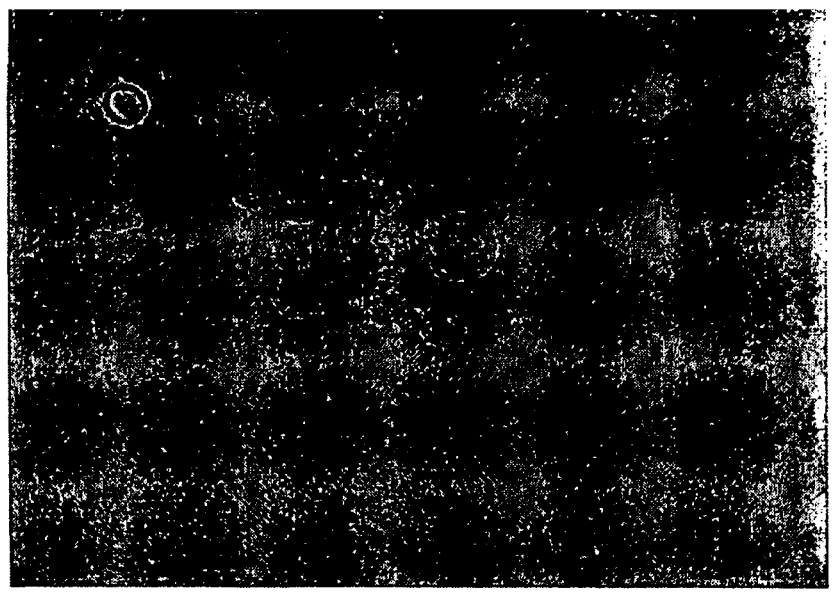
FIG. 1A shows a photograph of microspheres comprised of dihydrazide derivatized hyaluronate. The photograph was taken using a Zeiss microscope fitted with a Polaroid camera, type 347 film, with 25× magnification and normal illumination.

The present invention relates to microspheres comprised of hyaluronan derivatized with homobifunctional crosslinking groups. The homobifunctional crosslinking groups allow functionalized hyaluronan to be crosslinked and to serve as an intermediate for attachment of bio-effecting agents, drugs, peptides, fluorocarbons, oxygen-carrying agents, and other molecules of biological interest.

Hyaluronan possesses a number of characteristics that make its use as a drug carrier advantageous: it is biocompatible, non-immunogenic, subject to natural degradation by enzymes in the body, and possesses a number of functional groups such as OH, COOH and $CH_2OH$ that are amenable to covalent modification. Hyaluronan, however, is known to be unstable and undergoes degradation below about pH 2 and above about pH 9. The mild reaction conditions used in the invention avoid this degradation.

Moreover, the modified products show improved resistance to pH extremes.

Definitions

The term "hyaluronan" is commonly used to describe a series of naturally occurring, water soluble polysaccharides with anywhere from about 100 to about 10,000 alternating disaccharides of D-glucuronic acid and N-acetyl-D-glucosamine, and to describe degraded fractions of the same. The polymer is hydrophilic and highly viscous in aqueous solution at relatively low solute concentrations. Hyaluronic acid often occurs naturally as the sodium salt, sodium hyaluronate. Hyaluronic acid/sodium hyaluronate preparations are often referred to, and are referred to herein, as "hyaluronan" or "HA". Although the plural form "hyaluronans" may seem more appropriate, the discussion herein shall continue to use the singular form to refer to hyaluronan in its various forms, including its molecular fractions. Hyaluronan can be obtained from, e.g., Sigma, Genzyme, Lifecore, and Kraeber GMBH. Methods of preparing commercially available hyaluronic acid and salts thereof are well known in the art.

The term "hydrocarbyl" as used herein means the monovalent moiety obtained upon removal of a hydrogen atom from a parent hydrocarbon, or the divalent moitey obtained upon removal of two hydrogen atoms. Non-limiting examples of monovalent hydrocarbyls include alkyl, aryl, alkylaryl and arylalkyl The term "substituted hydrocarbyl" as used herein means the hydrocarbyl moiety as previously defined wherein one or more hydrogen atoms have been replaced with a chemical group which does not adversely affect the desired preparation of the product derivative. Representative of such groups are amino-,phosphino-, quaternary nitrogen (ammonium), quaternary phosphorous (phosphonium), hydroxyl, amide, alkoxy, mercapto, nitro, alkyl, halo, sulfone, sulfoxide, phosphate, phosphite, carboxylate, carbamate groups and the like.

As used herein, the term "about" or "approximately" means within 25%, preferably 15%, more preferably 5%, and most preferably 1% of the given value. Alternatively, the term "about" means the standard deviation or variance for a given value, if available.

The term "microsphere" is intended to mean a substantially spherical particle with a diameter of about 1 µm to about 500 µm. Microspheres need not be uniform in size. Microspheres may be solid or hollow and may encapsulate a pharmacologically active substance, a cosmetic agent, a biopolymer, or a growth factor. A microsphere may contain any substance, such as, but not limited to, pharmacologically active agents, polynucleotides, polypeptides, and cosmetic agents. Preferably, the substance is lipophilic when making microspheres using an oil-in-water emulsion; and hydrophilic when making microspheres using a water-in-oil technique.

The terms "pharmacologically active agent" or "cosmetic agent" as used herein refer to any chemical material, compound, or composition suitable for administration to humans and animals which provides any desired pharmacological or cosmetic effect.

The term "effective amount" of pharmacologically active agent or cosmetic agent refers to a nontoxic but sufficient amount of a compound to provide the desired effect and performance at a reasonable benefit/risk ratio attending any medical treatment.

The term "crosslinking agent" means any composition of matter that facilitates a cross linking reaction, i.e., that makes a crosslinking reaction occur more rapidly or efficiently. The term "crosslinker" means a molecule with two reactive groups, which can join to separate molecules or regions of a molecule by forming covalent bonds with two different functional groups on the molecule. As used herein, the term "bifunctional molecule" refers to a molecule with two reactive groups. The bifunctional molecule maybe homobifunctional or heterobifunctional. Homobifunctional molecules have at least two reactive functional groups, which are the same. Heterobifunctional molecules have at least two reactive functional groups, which are different.

The term "$pK_a$" is used to express the extent of dissociation or the strength of weak acids, so that, for example, the $pK_a$ of the protonated amino group of amino acids is in the range of about 12–13, in contrast to the $pK_a$ of the protonated amino groups of the dihydrazides useful herein, which is less than about 7.

The term "therapeutic drugs" is intended to include those defined in the Federal Food, Drug and Cosmetic Act. The United States Pharmacopeia (USP) and the National Formulary (NF) are the recognized standards for potency and purity for most common drug products.

The term "biocompatible" means non-toxic or non-damaging to human and non-human tissue.

The term "growth factor" means any composition of matter that specifically stimulates target cells to proliferate, differentiate, or alter their function or phenotype.

The term "biopolymer" means a molecule in which naturally occurring monomers, such as, for example, sugars or amino acids, are linked by covalent chemical bonds.

Preparation of HA Microspheres

In the present invention, microspheres are formed from hyaluronan derivatives. The HA crosslinking process involves the following steps: hyaluronate is mixed with a homobifunctional crosslinker; the pH is lowered to allow functionalization and crosslinking of HA to occur; and the pH of the suspension is raised after the crosslinking reaction is considered complete. In a preferred embodiment, an activating agent is also present to further facilitate the crosslinking reaction. An emulsifier is added to the HA solution before, during, or after, functionalization of HA. In a preferred embodiment, an emulsifier is added to the HA solution prior to lowering the pH. Once HA crosslinking has occured, and microspheres have been formed, the microspheres are dehydrated, dried and, optionally, sonicated. Each aspect of this process will be described more fully below.

Functionalization and crosslinking. The hyaluronate is functionalized by covalent attachment of homobifunctional crosslinking groups, such as pendant hydrazido groups. The hyaluronan is preferably functionalized at carboxyl groups of glucuronic acid moieties. Multiple crosslinking groups may be introduced into a hyaluronan polysaccharide. For example, the functionalization of hyaluronan with dihydrazide may be represented as Scheme 1 below:

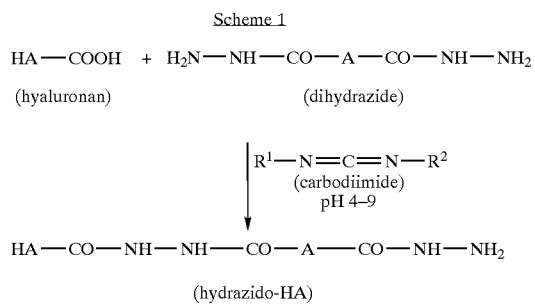

Crosslinkers include a reactive group for conjugation to a substituent; in the present case, for reaction with a carbonyl functional group on hyaluronic acid, and more particularly with a glucuronic acid functional group. As used herein, the term "reactive group" refers to a functional group on the crosslinker that reacts with a functional group on HA. The term "functional group" retains its standard meaning in organic chemistry. Carboxylic acids can be activated in the presence of carbodiimides, such as EDC, allowing for interaction with various nucleophilic reactive groups including primary and secondary amines. Alkylation of carboxylic acids to form stable esters can be achieved by interaction with sulfur or nitrogen mustards or crosslinkers containing either an alkyl or aryl aziridine moiety.

Dihydrazides useful in the invention can be represented by the following formula:

The symbol "A" in the dihydrazide formula may be considered to be a spacer group whose purpose is to allow one hydrazide to react with the hyaluronan carboxylate while leaving the second hydrazido group available for further chemical modification. "A" can be a hydrocarbyl, heterocarbyl, substituted hydrocarbyl substituted heterocarbyl, and the like. Suitable hydrocarbyls include alkyl, aryl, alkylaryl or arylalkyl and suitable heterohydrocarbyls also include oxygen, sulfur and/or nitrogen atoms, in addition to carbon atoms. An alkyl maybe branched or unbranched and may contain one to 20 carbons, or other carbon-sized atoms, preferably 2 to 10, more preferably, 4 to 8 carbons or carbon-sized heteroatoms, such as oxygen, sulfur or nitrogen. The alkyl maybe fully saturated or may contain one or more multiple bonds. The carbon atoms of the alkyl may be continuous or separated by one or more functional groups such as an oxygen atom, a keto group, an amino group, an oxycarbonyl group, and the like. The alkyl may be substituted with one or more aryl groups. The alkyl may, in whole or in part, be in form of rings such as cyclopentyl, cyclohexyl, and the like. The non-cyclic or cyclic groups described above may be hydrocarbyl or may include heteroatoms such as oxygen, sulfur, or nitrogen and maybe further substituted with inorganic, alkyl or aryl groups, including halo, hydroxy, amino, carbonyl, etc. Any of the alkyl groups described above may have double or triple bond(s). Moreover, any of the carbon atoms of the alkyl group may be separated from each other or from the dihydrazide moiety with one or more groups such as carbonyl, oxycarbonyl, amino, and also oxygen and sulfur atoms singly or in a configuration such as —S—S—, —O—CH$_2$—CH$_2$—O—, S—S—CH$_2$—CH$_2$— and NH(CH$_2$)$_n$NH—. Aryl substituents are typically substituted or unsubstituted phenyl, but may also be any other aryl group such as pyrrolyl, furanyl, thiophenyl, pyridyl, thiazoyl, etc. The aryl group maybe further substituted by an inorganic, alkyl or other aryl group including halo, hydroxy, amino, thioether, oxyether, nitro, carbonyl, etc. The alkylaryl or arylalkyl groups may be a combination of alkyl and aryl groups as described above. These groups may be further substituted as described above. Generally, to obtain dihydrazides, two hydroxy groups of a dicarboxylic acid are substituted with NH$_2$NH$_2$ yielding the dihydrazide.

Aliphatic dihydrazides can have the formula:

NH$_2$NHCO(CH$_2$)$_{n'}$CONHNH$_2$ wherein n'=1 to 18. Aliphatic dihydrazides useful in the invention include, for example, succinic (butandioic) (n'=2), adipic (hexanedioic)(n'=4) and suberic (octanedioic)(n'=6), oxalic (ethanedioic)(n'=0), malonic (propanedioic)(n'=1), glutaric (pentanedioic)(n'=3), pimelic (heptanedioic)(n'=5), azelaic (nonanedioic) (n'=7), sebacic (decanedioic)(n'=8), dodecanedioic, (n'=10), brassylic (tridecanedioic), (n'=11), etc. up to n'=20. Other dicarboxylic acids include, for example, maleic (HO$_2$CCH=CHCO$_2$H), fumaric (HO$_2$CCH=CHCO$_2$H) and aromatic dicarboxylic acids. Aromatic dihydrazides include terephthalic acid C$_6$H$_4$(COOH)$_2$. Some preferred dihydrazides are at least partially soluble in water and include succinic, adipic and suberic dihydrazides; also pimelic, sebacic, tridecane dioic, maleic, fumaric, isophthalic; as well as malonic, glutaric, and azelaic dodecanedioic dihydrazide. Another preferred dihydrazide is terephtalate dihydrazide (Lancaster, Pelham, NH), which requires an organic solvent for its solvation, such as, but not limited to, DMSO. Most preferred because of their commercial availability, are adipic and suberic dihydrazides, and also preferred are phthalic dihydrazide and dihydrazides containing oxa, thio, amino, disulfide (—CH$_2$—S—S—CH$_2$—), —S(CH$_2$)$_2$S—, —O(CH$_2$)$_n$O— or —NH(CH$_2$)$_n$NH—(n=2 to 4) groups. The preferred dihydrazides are also weak bases or weak acids having a pK$_a$ for the protonated form, less than about 8, preferably in the range of 1 to 7, and most preferably 2 to 6.

The carbodiimides useful in the invention may be represented by formula:

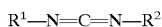

R$^1$—N=C=N—R$^2$ wherein R$^1$ and R$^2$ are each independently selected from the group consisting of hydrogen, hydrocarbyl of 1–25 carbon atoms, and including substituted-hydrocarbyl, alkoxy, aryloxy, alkaryloxy, and the like. The carbodiimides used in the invention are well known compounds, as represented by the formula given above. Carbodiimides having the above formula are preferred where R$^1$ and/or R$^2$ represent more specifically alkyl, cycloalkyl, aryl or substituted forms thereof. Most preferred are carbodiimides which are at least partly water soluble at ambient temperature and up to 80° C. Representative of a preferred class of monofunctional carbodiimides of the above formula are: 1-ethyl-3-(3-dimethylaminopropyl)carbodiimide (EDCI); N,N'-dicyclohexylcarbodiimide; N-allyl-N'-(β-hydroxyethyl)carbodiimide; N-α-dimethylaminopropyl)-N'tert-butylcarbodiimide; N-(α-dimethyl-aminopropyl)-N'-(β-bromoallyl)carbodiimide; 1-(3-dimethylaminopropyl)-3-(6-benzoylaminohexyl)-carbodiimide; cyclohexyl-β-(N-methylmorpholino)ethyl-carbodiimide-p-toluene-sulfonate (CMC); and the like.

The functionalization of hyaluronan with dihydrazides is preferably carried out under mild conditions including a pH of about 2 to about 8. A particularly preferred pH range is from about pH 3 to about 5. The hyaluronate is dissolved in water, which may also contain water-miscible solvents such as dimethylformarnide, dimethylsulfoxide, and hydrocarbyl alcohols, diols, or glycerols. In one embodiment, at least one molar equivalent of dihydrazide per molar equivalent carboxyl hyaluronate is added. For maximum percentage functionalization, a large molar excess of the dihydrazide (e.g., 10–100 fold) dissolved in water or an aqueous-organic mixture is added and the pH of the reaction mixture is adjusted by the addition of dilute acid, e.g., HCl. A sufficient molar excess (e.g., 2 to 100 fold) of carbodiimide reagent dissolved in water, in any aqueous-organic mixture, or finely-divided in solid form, is then added to the reaction mixture. The hyaluronate and dihydrazide should preferably be mixed together before addition of the carbodiimide. An increase in pH maybe observed after addition of the carbodiimide and additional dilute HCl or other acid may be added to adjust the pH. Alternatively, a suitable buffer, such as Bis-Tris, may be included. In such cases, a more concentrated acid solution may be required to lower the pH of the solution (or emulsion, if emulsifier has been added (see below)). The reaction is allowed to proceed at a temperature of about 0° C. to about 100° C. (e.g., just above freezing, 0° C., to just below boiling (100° C.)), preferably at or near room temperature for purposes of convenience. The time of the reaction is from about 0.5 to about 48 hours, preferably about one to about five hours. Polymerization is a function of the chosen reactants and their concentrations, pH, temperature, and all other variables that affect chemical reaction rates. In the case where an emulsifier has been added, agitation of the emulsion also affect the polymerization rate. Periodically (e.g., once every 10 minutes during the first hour; thereafter every hour) the pH is measured, using either pH test strips (e.g., from EM Science) or a pH meter with an electrode, and adjusted, if necessary, by small additions of acid to maintain the pH within the chosen range. The crosslinking reaction may optionally be stopped by, e.g., increasing the pH to within the range of about 7 to about 9, for example by adding ammonium hydroxide. After the crosslinking reaction is complete, the pH may be adjusted to an approximately neutral range.

Formation of Microspheres. An emulsion technique is used to form microspheres from functionalized hyaluronate. An emulsifier, such as, but not limited to, Span 60 (obtained from Aldrich Co.) can be added to the HA solution before, during, or after the derivatization reaction. In a preferred embodiment, an emulsifier is added to an aqueous solution of HA, a hydrazide, and a carbodiimide, prior to lowering pH.

Preferably, the emulsifier is first dissolved in a solvent. In one embodiment, the emulsifier concentration in the organic solvent ranges from about 0.01–10%, or, more preferably, from 1–2% (weight/volume); and about an equal volume of the solvent containing emulsifier is added to the HA solution. However, for each specific set of chosen reagents and experimental conditions the appropriate relative amounts of emulsifier, solvent, and HA solution may vary, but can be optimized by one skilled in the art. Also, suitable solvents and emulsifier concentrations may be chosen based upon, e.g., toxicity and or emulsifier characteristics. Preferably, the solvent is anon-water-miscible liquid. Preferred, although non-limiting, non-water-miscible liquids include toluene (e.g, from Aldrich Co.), silicone oil (Dow Corning 200/0.65 cts), mineral oils of suitable viscosity, and vegetable oils such as olive oil. A solvent such as silicone oil may result in microspheres less prone to aggregation. In addition, hydroxypropyl methylcellulose has been identified as an additive allowing microspheres to be recovered after drying with minimal agglomeration.

The emulsifier is advantageously added slowly to a HA solution stirred using, e.g., a direct drive mixer (obtained from Cole-Parmer) with a metal propeller, or any other suitable mixer. The stirring rate may range from about 60 rpm to about 2000 rpm. Preferably, a stirring rate of about 800 rpm is used. For purposes of convenience, the temperature of the HA solution is preferably at or near room temperature, but other temperatures ranging from about 0° C. to about 100° C. (e.g., just above freezing, 0° C., to just below boiling (100° C.)), may be employed if so desired. After the addition of the organic phase, an emulsion is effected. The formed globules can be observed using, e.g., a microscope at about 40× magnification. If the emulsifier is added prior to HA derivatization, the pH of the emulsion is brought to the chosen pH range (see above), and maintained by adding small amounts of dilute acid, to allow both intramolecular and intermolecular crosslinking to occur within and between derivatized hyaluronate molecules until the crosslinking reaction is considered complete.

Thereafter, the suspension maybe dehydrated by the addition of a liquid, preferably an alcohol. The alcohol such as, but not limited to, isopropanol (obtained from Aldrich Co.). The suspension is separated into two layers and the organic solvent layer is removed. Isopropanol (or another dehydrating alcohol) is added to the solution, and, after mixing, the isopropanol is removed. If desired, additional isopropanol maybe added, and the solution stirred overnight. Depending, for instance, on the choice of oil or solvent, some aggregation of microspheres may occur, as shown in the Examples below. In some cases, aggregation can be reversed to some degree by sonicating the suspension for a suitable length of time, e.g., about 45 minutes. As shown in the Examples below, the appearance as well as the aggregation characteristics of a microspheres preparation maybe influenced by the choice of solvent. Once a phase change is effected, microspheres will settle from the vessel when stirring is terminated. The microspheres may be collected by sedimentation under gravity, centrifugation, or filtration, and, optionally, dried at an elevated temperature.

Use of HA Microspheres

Microspheres may contain any substance that can be dissolved in an oil phase when making microspheres using an oil in water emulsion, or dissolved in the water phase when using a water in oil technique. In the case of the microspheres of the invention, substances to be incorporated have to be present prior to lowering the pH to initiate HA polymerization. However, once the microspheres have been formed, they may also be useful as carriers of substances that will adhere or be attached to pendant hydrazide groups on the spheres. Thus, the microspheres of this invention can be used as carriers for a wide variety of releasable biologically active substances having curative or therapeutic value for human or non-human animals. Included among biologically active materials that are suitable for incorporation into the microspheres of the invention are therapeutic drugs, e.g., anti-inflammatory agents, anti-pyretic agents, steroidal and non-steroidal drugs for anti-inflammatory use, hormones, growth factors, contraceptive agents, antivirals, antibacterials, antifimgals, analgesics, hypnotics, sedatives, tranquilizers, anti-convulsants, muscle relaxants, local anesthetics, antispasmodics, antiulcer drugs, peptidic agonists, sympathiomimetic agents, cardiovascular agents, antitumor agents, oligonucleotides and their analogues, etc. Examples of preferred active substances are all anti-inflammatory compositions, including, but not limited to, ibuprofen, naproxen, ketoprofen and indomethacin. Other preferred biologically active substances are peptides that are naturally occurring, non-naturally occurring or synthetic polypeptides or their isosteres, such as small peptide hormones or hormone analogues and protease inhibitors. Also preferred are spermicides, antibacterials, antivirals, antifimgals and antiproliferatives such as fluorodeoxyuracil and adriamycin. These substances are all known in the art.

The actual preferred amounts of active compound in a specified case will vary according to the specific compound being utilized, the particular compositions formulated, the mode of application, and the particular situs and organism being treated. Dosages for a given host can be determined using conventional considerations, e.g. by customary comparison of the differential activities of the subject compounds and of a known agent, e.g., by means of an appropriate convention pharmacological protocol.

The pendant hydrazido group of the derivatized hyaluronan of the microspheres may be used for the coupling of compounds to hyaluronan. For example, drugs may be covalently attached through the intermediacy of hydrolytically and/or enzymatically labile bonds, which allows for the preparation of controlled release formulations. Such labile linkages include ethers, imidates, thioimidates, esters, amides, thioethers, thioesters, thioamides, carbamates, disulfides, hydrazides, hydrazones, oxime ethers, oxime esters and amines. Carboxylate-containing chemicals such as the anti-inflammatory drugs ibuprofen or hydrocortisone-hemisuccinate can be converted to the corresponding N-hydroxysuccinimide (NHS) active esters and can further react with a primary amino group of the dihydrazides. Non-covalent entrapment of a pharmacologically active agent in the microspheres is also possible. Electrostatic or hydrophobic interactions can facilitate retention of a pharmaceutically active agent in the microspheres. For example, the hydrazido of the invention can non-covalently interact, e.g., with carboxylic acid-containing steroids and their analogs, and anti-inflammatory drugs such as Ibuprofen (2-(-4-iso-butylphenyl)propionic acid). The protonated hydrazido group can form salts with a wide variety of anionic materials such as proteins, heparmn or dermatan sulfates, oligonucleotides, phosphate esters, and the like.

The microspheres of the invention may be directly labeled for in vivo imaging purposes, such as CAT, PET, and MRI scanning. Labels for use in the invention include colloidal gold, colored latex beads, magnetic beads, fluorescent labels (e.g., fluorescene isothiocyanate (FITC), phycoerythrin (PE), Texas red (TR), rhodamine, free or chelated lanthanide series salts, especially $Eu^{3+}$, to name a few fluorophores), chemiluminescent molecules, radioisotopes ($^{125}I$, $^{32}P$, $^{35}S$, chelated Tc, etc.) ormagnetic resonance imaging labels.

Materials that have been incorporated into the microspheres can be subject to sustained release by chemical, enzymatic and physical erosion of the microsphere and/or the covalent hyaluronate-drug linkage over a period of time, providing improved therapeutic benefits of the compounds. Sustained release is particularly useful with anti-inflammatories, anti-infectives, sperimicidal and anti-tumor agents.

The microspheres of this invention can incorporated into a formulation for the purpose of administration to humans and animals. Suitable formulations include, but are not limited to, solutions, suspensions, emulsions, creams, ointments, powders, liniments, salves, aerosols, etc., which are, if desired, sterilized or mixed with auxiliary agents, e.g., preservatives, stabilizers, wetting agents, buffers, or salts for influencing osmotic pressure, etc. The microspheres of this invention can be employed in admixture with conventional excipients, i.e., pharmaceutically acceptable organic or inorganic carrier substances suitable for parenteral or topical application which do not deleteriously react with the active compounds. Suitable pharmaceutically acceptable carriers include, but are not limited to, water, salt solutions, alcohols, gum arabic, vegetable oils, benzyl alcohols, polyethylene glycols, gelatine, carbohydrates such as lactose, amylose, or starch, magnesium stearate, talc, silicic acid, viscous paraffin, perfume oil, fatty acid monoglycerides and diglycerides, pentaeryffiritol fatty acid esters, hydroxymethyl cellulose, and polyvinyl pyrrolidone, merely to name a few. The pharmaceutical preparations can be sterilized, and if desired, mixed with auxiliary agents, e.g., lubricants, preservatives, stabilizers, wetting agents, emulsifiers, salts for influencing osmotic pressure, buffers, coloring, flavoring and/or aromatic substances and the like, which do not deleteriously react with the active compounds. The pharmaceutical preparations can also be combined where desired with other active agents, e.g., vitamins.

Hyaluronic acid is a useful moisturizing and lubricating agent in skin creams, shampoos, and a variety of cosmetics. For cosmetic applications, additional biocompatible or biologically inert materials may be incorporated into the hyaluronan microspheres of the invention. Additional cosmetic materials include humectants, i.e., substances having affinity for water such as glycerine, propylene glycol or isopropanolpropylene glycol; organic or inorganic salts such as quaternary ammonium compounds and zinc salts; enzymes; peptides; alcohols such as benzyl alcohol or lower aliphatic alcohols; polymer latices; fillers such as silica and talc; oils such as mineral oil, castor oil and petrolatum; wetting or dispersing agents or surfactants such as block copolymers of ethylene oxide and propylene oxide to reduce adherence to skin; dyes; fragrances; pigments; antisolar or UV absorbing agents such as actinoquinol, anthranilates, cinnamates, benzyl and homomenthyl salicylate; para-aminobenzoic acid and its ester derivatives; zinc oxide and titanium dioxide; topical medicaments such as methylsalicylate, nicotinates, capsaicin and menthol; antiacne medicaments such as benzoyl peroxide, resorcinol and retinoic acid; topical antibacterials such as silver sulfadiazine, tetracycline and cefazolin; skin hydrating agents such as sodium pyrrolidine carboxylic acid; and other compounds such as fatty acids having about 2 to about 24 carbon atoms, which change the rheological properties of the modified hyaluronan. As is apparent from this list of biocompatible materials, the microspheres of the invention may be used for cosmetic treatments and dressings.

The following non-limiting examples further illustrate the invention.

EXAMPLES

Example 1
Preparation of HA Microspheres

One opening of a 500 ml organic reaction kettle (with interchangeable covers and four openings) was fitted with a safe-lab stirrer bearing. Six-hundred mg (1.44 mmol) of sodium hyaluronate (HA), 378 milligrams (2.16 mmol) of adipic dihydrazide (ADH), and 100 ml of water were placed in the kettle. The HA and ADH were completely dissolved in the water, resulting in the formation of a viscous liquid with a pH of 6 to 7. Two-hundred seventy-eight mg (1.44 mmol) of 1-ethyl-dimethylamino-propyl carbodiimide (EDCI) in 10 ml of water was added to the kettle. The mixture was stirred for five minutes.

One-hundred ml of toluene solution containing 1.5% w/v Span 60 was added to the kettle and an emulsion was formed by vigorous stirring at 800–1000 rpm. After the emulsion was formed, the pH of the suspension was decreased to between 4 and 5 using 1N HCl. The crosslinking reaction was continued for six hours. The pH was then raised to between 7 and 9 using 10% (w/v) ammonium hydroxide.

One-hundred ml of the dehydrating agent isopropanol was added to the suspension and the mixture was stirred for approximately 10 minutes. The suspension was separated into two layers. The supernatant contained toluene, which was removed. An additional 100 ml of isopropanol was added to the suspension. The isopropanol was decanted and an additional 150 ml of isopropanol was added and the suspension was stirred at 500 rpm overnight.

Figure 1B:
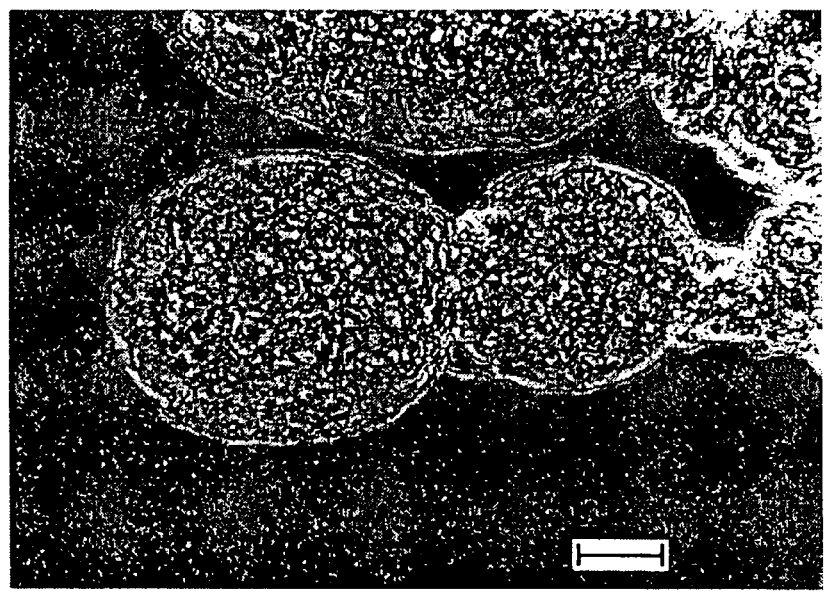
FIG. 1B shows a photograph of microspheres comprised of dihydrazide derivatized hyaluronate. The photograph was taken using a Zeiss microscope fitted with a Polaroid camera, type 347 film, with 25× magnification and phase contrast illumination.
Figure 2A:
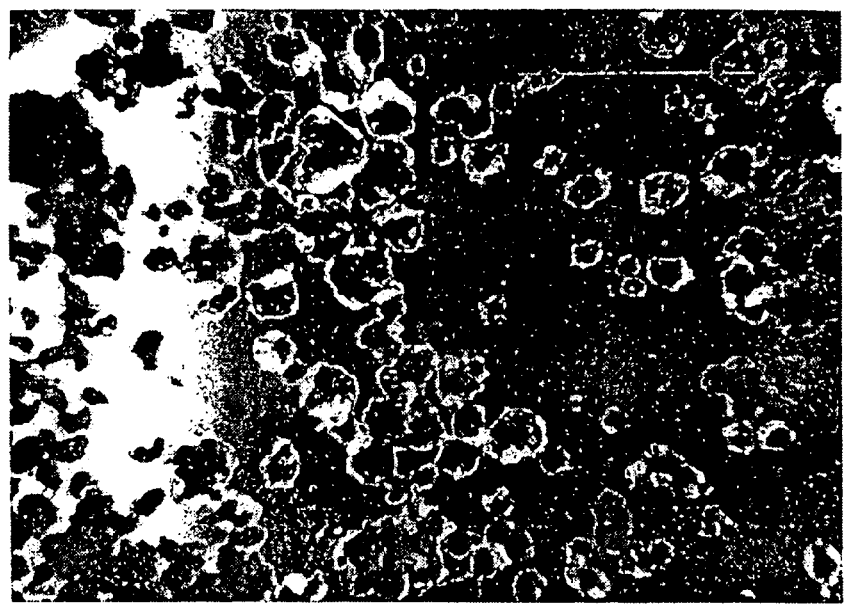
FIG. 2A shows a photograph of desiccated FITC-labeled microspheres, prepared as described in Example 2 (see below). The photograph was taken using a Zeiss microscope fitted with a Polaroid camera, type 347 film, with 25× magnification and phase contrast illumination.
Figure 2B:
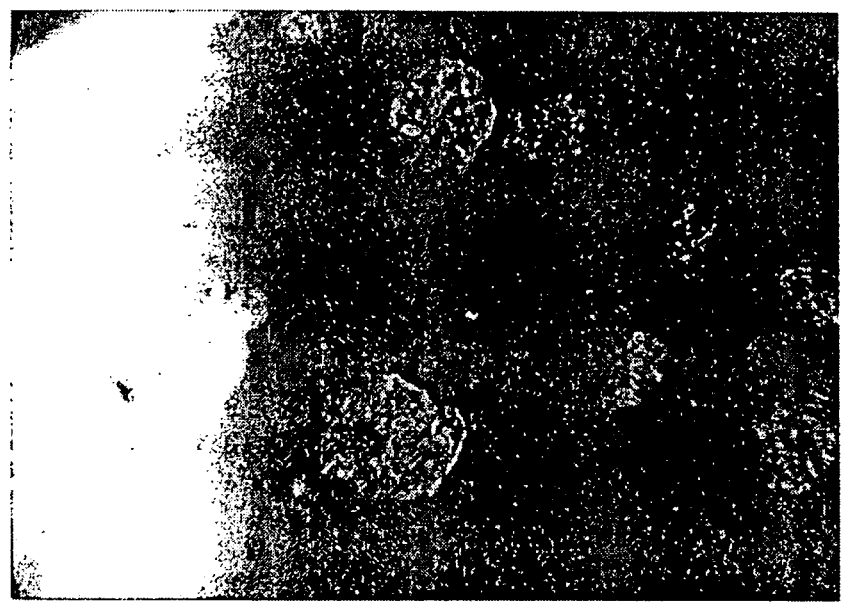
FIG. 2B shows a photograph of FITC-labeled microspheres in water. FITC-labeled microspheres were prepared as described in Example 2 (see below), and thereafter resuspended in water for several minutes. The photograph, taken using identical conditions to those described in FIG. 2A, shows the change in size of the microspheres, and confirms their resistance to dissolution after crosslinking
Figure 3A:
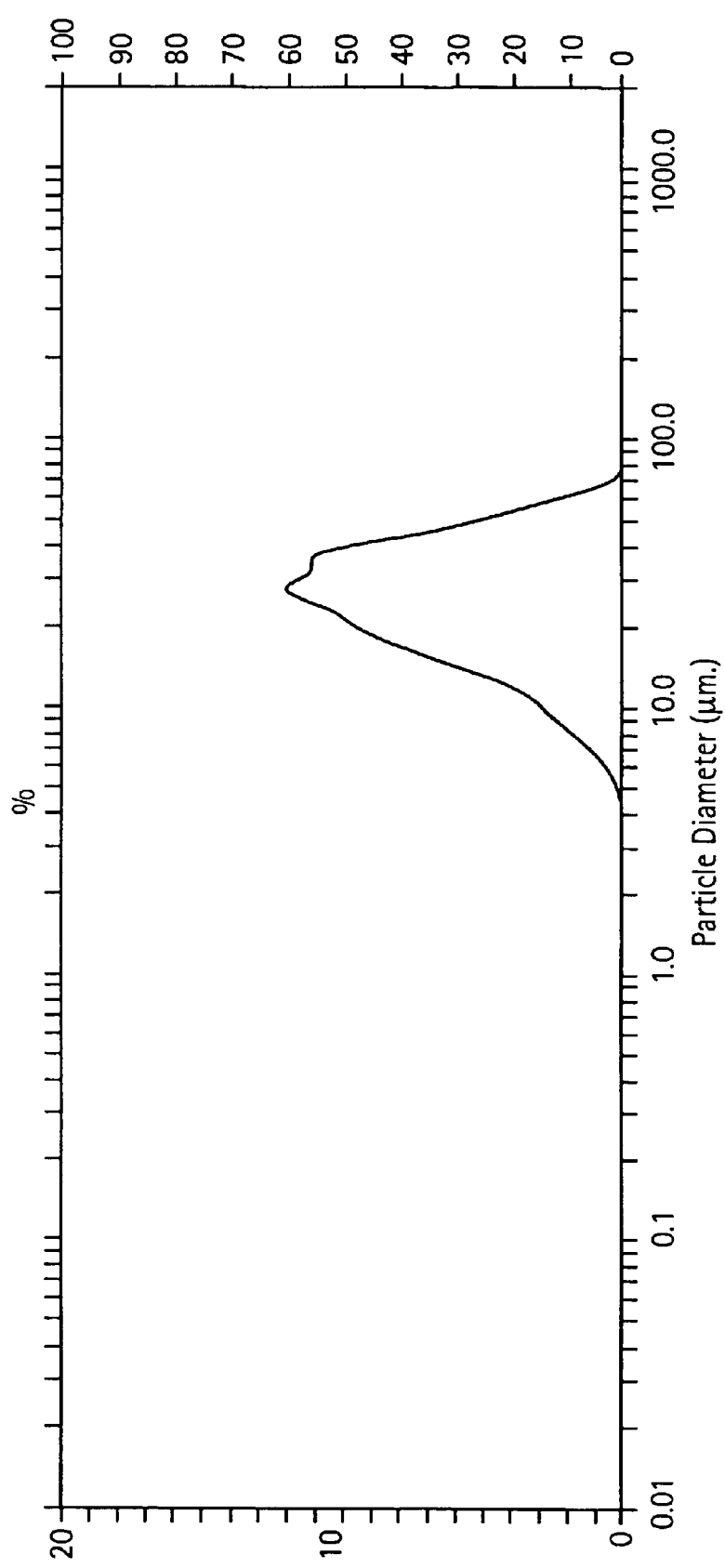
FIG. 3A depicts the size distribution of microspheres suspended in 100 ml isopropylalcohol, analyzed as described in Example 3 (see below).
Figure 3B:
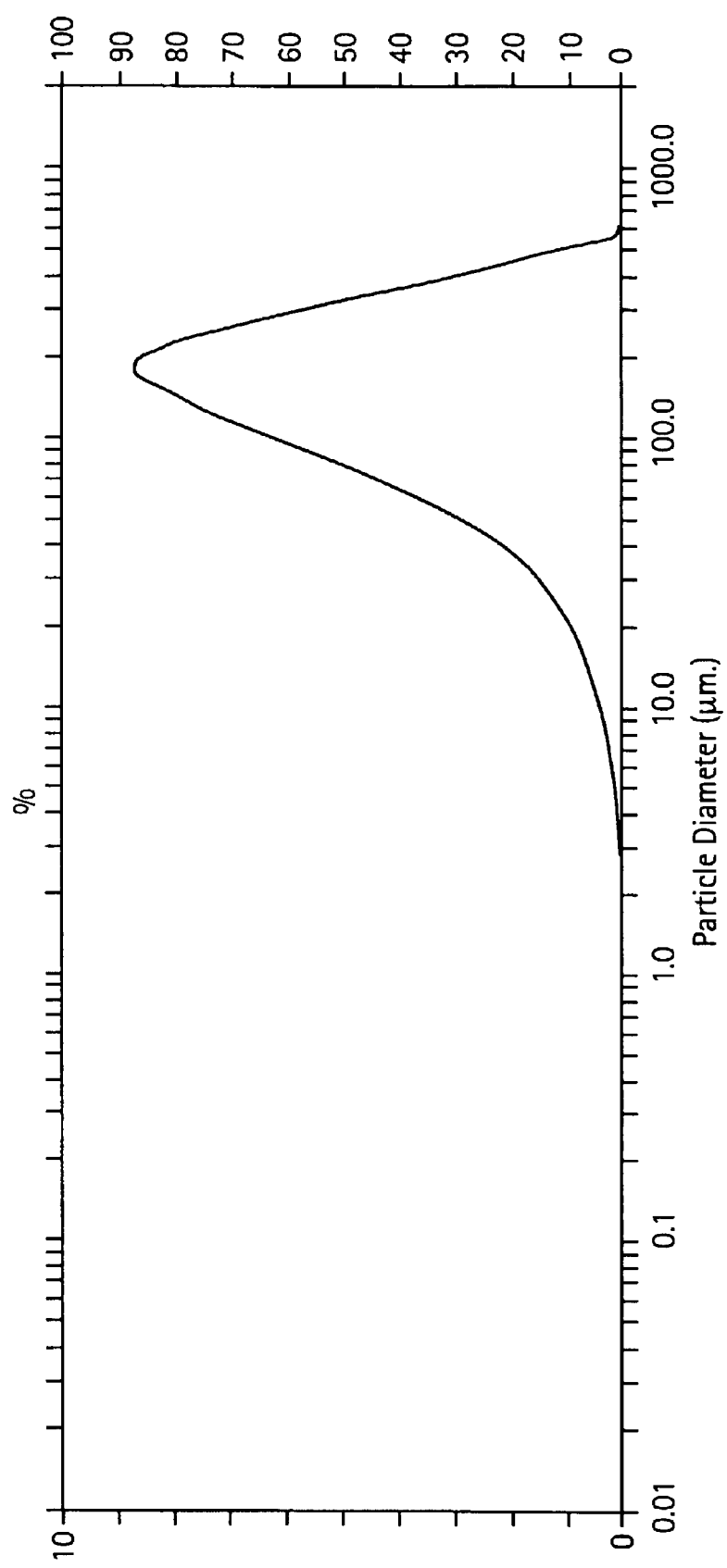
FIG. 3B depicts the size distribution of microspheres recovered from isopropylalcohol and resuspended in distilled water for 7 min prior to size distribution analysis.

The microspheres were examined with an optical microscope (FIGS. 1A, 1B). Some microspheres adhered together to form large particles. The large microsphere particles were sonicated in the isopropanol suspension for 45 minutes to break the large particles into individual microspheres. The suspension was filtered to recover the microspheres and the microspheres were dried at 37° C.

Example 2
Preparation of FITC-labeled HA Microspheres

Microspheres containing FITC-labeled bovine serum albumin (BSA) were prepared for studies of release of this marker protein from the spheres under various conditions. Essentially, experimental conditions were similar to those described in Example 1, except for the addition of FITC-labeled BSA to the HA solution, at a concentration of 10 mg/100 ml HA solution. After dissolution and addition of all materials, polymerization was effected as described. The microspheres were thereafter washed by repeated sedimentation and resuspension in isopropyl alcohol. The labeled microspheres were recovered by sedimentation and allowed to dry in an oven for 24 h at 37° C.

Example 3
Determination of Microsphere Size Distribution

Particle size distribution was determined using a Malvern Mastersizer S instrument, operated at ambient temperature, after adjusting the particle suspension obscurescence to approximately 10%.

Example 4
The Effect of pH on the Crosslinking Rate

The effect of pH on the crosslinking rate of sodium hyaluronate (HA) with adipic dihydrazide (ADH) in the presence of 1-ethyl-dimethylaminopropyl carbodiimide (EDCD) was determined at room temperature. The results of the experiment are illustrated in Table 1. Sodium hyaluronate and adipic dihydrazide (in the amount shown in Table 1) were dissolved in water, and EDCI (in the amount shown in Table 1) was added to the mixture. The molar ratio of HA to ADH to EDCI was approximately 1 to 1.5 to 1, respectively. The pH was adjusted to either 10, 9, 8, 7, 6, 5, 4, or 3 with dilute NaOH or HCl. Crosslinking reactions were continued for 1, 12, and 24 hours and at each time point the viscosity of the solutions were noted. A viscous liquid indicated that crosslinking had not occurred, whereas an unmovable, solid gel indicated extensive crosslinking. At pH 10, crosslinking did not occur even after 24 hours, and the viscosity of the solution remained unchanged. At pH 7, 8, and 9 the viscosity of the solutions increased from 1 to 12 to 24 hours, but the solutions were still rather liquid after 24 hours. At pH 4, 5, and 6 the viscosity of the solutions also increased from 1 to 12 to 24 hours, but the solutions were more viscous at each time point than were the solutions at pH 7,8, and 9. At pH 3, the solution became an unmovable gel after only seven minutes.

TABLE 1

The Effect of Time and pH on the Crosslinking Rate

| HA (mg) | H₂O (g) | ADH (mg) | EDCI (mg) | pH | 1 hr | 12 hr | 24 hr |
|---|---|---|---|---|---|---|---|
| 17.8 | 2.9985 | 12.0 | 8.1 | 10 | — | — | — |
| 18.1 | 2.9985 | 12.5 | 8.5 | 9 | * | ** | *** |
| 17.8 | 3.0280 | 11.6 | 8.6 | 8 | * | ** | *** |
| 17.9 | 3.0374 | 11.8 | 8.3 | 7 | * | ** | *** |
| 18.1 | 2.9958 | 13.2 | 8.4 | 6 | ** | *** | **** |
| 18.0 | 2.9923 | 13.3 | 8.5 | 5 | ** | *** | **** |
| 17.9 | 3.0018 | 11.8 | 8.4 | 4 | ** | *** | **** |
| 18.3 | 2.9871 | 12.6 | 8.6 | 3 | solid gel | solid gel | solid gel |

The viscosity of the solution is indicated by the number of asterisks, with more asterisks indicating a more viscous solution.

Example 4
Polymerization of Microspheres Containing FITC-BSA in Silicone Fluid Dow 200 Using ADH and Cosmetic Grade HA.

Three-hundred mg HA and 0.42 g Bis-Tris was dissolved in 100 ml water with slow stirring, using flat impeller. Three-hundred mg ADH was added and dissolved. About 1 mg FITC-BS was added and mixed. Twenty mg hydroxypropyl methylcellulose (HPMC, Sigma) was added to 15 ml water with heating. The cloudy suspension was added to the HA reaction mix. The remainder of the suspension was recovered by adding reaction mixture to the vial-mixture and add remainder to vessel. Thereafter, pH was adjusted to about 4.0 with 1 N HCl (pH strips, about 30 drops). Three-hundred mg EDCI was dissolved in 10 ml water, added immediately to the reaction mixture, and mixed for about 2 min.

The mixture was then emulsified at approximately 600 rpm with 100 ml Silicone Dow Coming 200 fluid, containing 1% (w/w) Span 80, and allowed to polymerize for 5 h at room temperature. After 2 hours, pH was adjusted to about 5 with 1 N HCl (about 10 drops). After 5 hours, pH was adjusted to about 9–10 with 1N NaOH (about 30 drops). The remainder of the emulsion was stirred, with moderate reduction in speed, for about 30 min. The emulsion was thereafter decanted into 4×50 ml centrifuge tubes, and centrifuged at 1500 rpm for 20 min. Three layers were obtained: upper (oil), middle (emulsion) and minimal lower (aqueous). The upper oil layer was decanted, the middle emulsion layer was scooped out, and the aqueous layer was re-centrifuged at room temperature. The $1^{st}$ cut emulsion layer and the $2^{nd}$ cut emulsion layer (creamiest portion-small amount) was added to IPA as follows. The emulsion layer was added, scoopula wise, to 250 ml IPA 25 ml water, adjusted to about pH 7 by the addition of 1 N NaOH, and stirred at about 600 rpm. The pH was checked, and adjusted to about 7 with 1 N HCl. The emulsion was stirred for about 30 min at 700 rpm, and thereafter left overnight without stirring. The alcohol suspension was centrifuged at 1500 rpm for about 20 min at room temperature, and the tubed drained well. About half of the sedimented material was suspended in several milliliters of IPA, and the other half in several milliliters of water.

Figure 4:
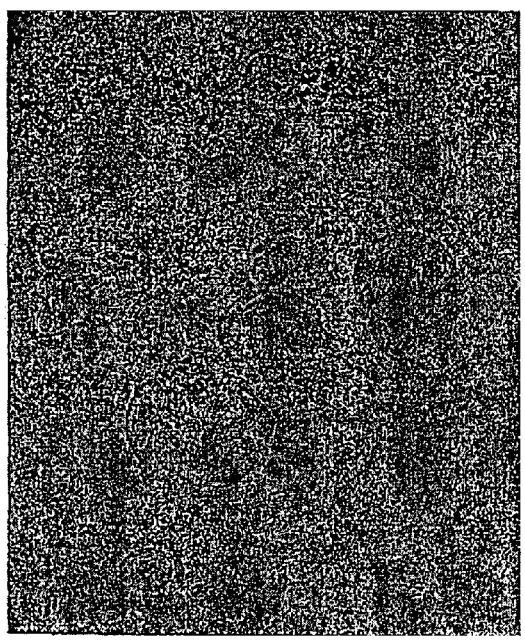
FIG. 4 shows a photograph of microspheres prepared from silicone oil. See Example 4. The photograph was taken using a Zeiss microscope fitted with a Polaroid camera, with 100× magnification.

The water suspension got thick and sticky and contained spheres (See FIG. 4). The alcohol suspension remained slightly granular and contained spheres. The suspensions were dried at about 37° C. in separate watch glasses. The IPA dried suspension (about 3 hrs) was flakey but could be re-suspended in water to give microspheres with large size variation with lots of debris. There was not a lot of aggregation. Spheres dried from aqueous suspension and resuspended in water did not reassume the morphology expected. Swelled material resembled gel fragments of an irregular shape and were somewhat amorphous. HPMC was used because it had been identified as an additive that would allow microspheres to be recovered after drying with minimal agglomeration. However, as this experiment shows, what was more important was whether the microspheres were dried from aqueous or alcohol suspensions.

Example 5
Effect of Various Parameters on Microsphere Preparation

In this Example, hydrophilic hyaluronate sodium microspheres were prepared from the HA-ADH-EDCI crosslinking reaction by inversion emulsion polymerization. Table 2 lists the various parameters applied for each preparation, as well as the weight and appearance of the microspheres formed.

TABLE 2

Preparations of sodium hyaluronate microspheres

| | Preparation No. | | | | | | |
|---|---|---|---|---|---|---|---|
| | 1 | 2 | 3 | Albumin 4 | 5 | 6 | 7 |
| Water Phase: | | | | | | | |
| HA (mg) | 600 | 600 | 600 | 600 | 600 | 600 | 600 |
| ADH (mg) | 376 | 377 | 377 | 366 | 377 | 377 | 377 |
| Water (ml) | 100 | 100 | 100 | 100 | 100 | 100 | 100 |
| EDCI (mg) | 277 | 277 | 277 | 346 | 346 | 346 | 246 |
| Initial PH | 6–7 (Buffer) | 6–7 | 6–7 | 6–7 | 6–7 | 6–7 | 6–7 |
| HA:ADH:EDCI, (mmol ratio) | 1:1.5:1 | 1:1.5:1 | 1:1.5:1 | 1:1.5:1.25 | 1:1.5:1.25 | 1:1.5:1.25 | 1:1.5:1.25 |
| Oil Phase: | | | | | | | |
| Span 60 (g) | 1.5 | 1.5 | 1.5 | 1.5 | 1.5 | 1.5 | 1.5 |
| Toluene (ml) | 100 | 100 | 100 | 100 | 100 | 100 | 100 |
| Stirring rate (rpm) | 800 | 800 | 800 | 700 | 600 | 600 | 600 emul. 1 hr |
| Reaction time (h) | 4 | 6 | 6 | 6 | 4 | 4 | 4 |
| Final pH (10% NH₄OH) | 6–7 → 6–7 | 3 → 10 | 6–7 | 9–10 | 6–7 | 3 → 7 | 3 → 4 |

TABLE 2-continued

Preparations of sodium hyaluronate microspheres

| | Preparation No. | | | | | | |
|---|---|---|---|---|---|---|---|
| | 1 | 2 | 3 | Albumin 4 | 5 | 6 | 7 |
| Dehydrating agent; IPA (ml) | 2 × 150 | 2 × 100 | 2 × 150 | 2 × 150 | 2 × 150 | 250, 150 | 250, 150 |
| Particles & shape | Sphere & Aggregated beads | gel & beads | beads & Particles | Beads & particles | Beads & particles | Beads & Aggregated beads | Microspheres & particles |
| weight (g) | 0.2860 | 0.7734 | 0.6667 | 0.6119 | 0.7149 | — | 0.6548 |

The present invention thus relates to microspheres comprising hyaluronan functionalized with a homobifunctional crosslinker at glucuronic acid sites and methods of making such microspheres. The derivatized hyaluronan microspheres have useful pharmacological and cosmetic applications as delivery vehicles for active pharmacological and cosmetic agents.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all numerical values are approximate, and provided for description.

All patents, patent applications, publications, and other materials cited herein are hereby incorporated herein reference in their entireties. In case of conflicting terminology, the present disclosure controls.

We claim:

1. A microsphere comprising hyaluronan derivatized with a crosslinker at carboxyl groups of glucuronic acid sites of the hyaluronan, wherein the crosslinker is a dihydrazide having the formula:

$$H_2N-NH-CO-A-CO-NH-NH_2$$

wherein A is a substituted hydrocarbyl, unsubstituted hydrocarbyl, substituted heterocarbyl or unsubstituted heterocarbyl moiety and wherein the derivatized hyaluronan is crosslinked intramolecularly and intermolecularly.

2. The microsphere of claim 1, wherein said substituted hydrocarbyl, unsubstituted hydrocarbyl, substituted heterocarbyl or unsubstituted heterocarbyl moiety has one to twenty carbons or heteroatoms.

3. The microsphere of claim 2, wherein A is a heterocarbyl having heteroatoms selected from the group consisting of nitrogen, oxygen, and sulfur.

4. The microsphere of claim 2, wherein the carboxyl groups of the glucuronic acid residues have been activated with a carbodiimide.

5. The microsphere of claim 4, wherein the carbodiimide is 1-ethyl-dimethylaminopropyl carbodiimide.

6. The microsphere of claim 1, where the microsphere is formed by mixing hyaluronan and the dihydrazide in an aqueous solution, adding a substantially non-water miscible liquid and an emulsifying agent to form a water in oil type-emulsion, and lowering the pH of the emulsion.

7. The microsphere of claim 1, further comprising a component that is incorporated into the microsphere.

8. A method of making a functionalized hyaluronic acid microsphere comprising mixing hyaluronic acid and a dihydrazide with a crosslinking activator in an aqueous solution, adding a substantially non-water miscible liquid and an emulsifying agent to form an oil in water-type emulsion, and lowering the pH of the emulsion to allow intramolecular and intermolecular crosslinking to occur, wherein the dihydrazide has the formula:

$$H_2N-NH-CO-A-CO-NH-NH_2$$

and wherein A is a substituted hydrocarbyl, unsubstituted hydrocarbyl, substituted heterocarbyl or unsubstituted heterocarbyl moiety.

9. The method of claim 8, wherein the pH of the emulsion is lowered to the range from about pH 7 to about pH 4.

10. The method of claim 8, further comprising dehydrating the microspheres after they have formed.

11. The method of claim 8, wherein the crosslinking activator is a carbodiimide.

12. The method of claim 8, wherein at least one molar equivalent of a dihydrazide is added per molar equivalent of glucuronic acid groups on the hyaluronic acid.

13. The method of claim 8, wherein as least one molar equivalent of a carbodiimide is added per molar equivalent of glucuronic acid groups on the hyaluronic acid.

14. The method of claim 8, wherein said substituted hydrocarbyl, unsubstituted hydrocarbyl, substituted heterocarbyl or unsubstituted heterocarbyl moiety has one to twenty carbons or heteroatoms.

15. The method of claim 8, wherein A is a substituted heterocarbyl or an unsubstituted heterocarbyl having heteroatoms selected from the group consisting of nitrogen, oxygen, and sulfur.

16. A pharmaceutical or cosmetic formulation comprising a pharmacologically effective amount of the microsphere of claim 7 and an acceptable carrier, excipient, or diluent.

17. A method of administering microspheres to a human or animal comprising administering a pharmacologically effective amount of the pharmaceutical or cosmetic formulation of claim 16.

* * * * *